(12) United States Patent
Krishnaiyer Raman et al.

(10) Patent No.: US 11,647,917 B2
(45) Date of Patent: May 16, 2023

(54) INTELLIGENT MODEL BASED PATIENT POSITIONING SYSTEM FOR MAGNETIC RESONANCE IMAGING

(71) Applicant: KONINKLIJKE PHILIPS N.V., Eindhoven (NL)

(72) Inventors: Sivaramakrishnan Krishnaiyer Raman, Bangalore (IN); Girish Bogadi Eswara Prasad, Bangalore (IN); Kumar Raja Gattamaneni, Bangalore (IN); Girish Kumar Chegu, Bangalore (IN); Prashanth Honnemaradahalli Shivamurthy, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 1069 days.

(21) Appl. No.: 16/341,201

(22) PCT Filed: Oct. 12, 2017

(86) PCT No.: PCT/EP2017/076137
§ 371 (c)(1),
(2) Date: Apr. 11, 2019

(87) PCT Pub. No.: WO2018/069479
PCT Pub. Date: Apr. 19, 2018

(65) Prior Publication Data
US 2020/0178839 A1   Jun. 11, 2020

(30) Foreign Application Priority Data
Oct. 12, 2016   (IN) .............................. 201641034779

(51) Int. Cl.
*A61B 5/055*      (2006.01)
*G06T 7/33*       (2017.01)
(Continued)

(52) U.S. Cl.
CPC ............ *A61B 5/055* (2013.01); *A61B 5/1114* (2013.01); *A61B 5/7445* (2013.01);
(Continued)

(58) Field of Classification Search
CPC ..... A61B 5/1114; A61B 5/7445; A61B 5/055; G06T 3/0093; G06T 7/344;
(Continued)

(56) References Cited

U.S. PATENT DOCUMENTS 10,172,574 B2    1/2019  Schafer et al.
2007/0038070 A1  2/2007  Tank
(Continued)

FOREIGN PATENT DOCUMENTS

CN    101019765 A    8/2007
CN    103431863 A   12/2013

OTHER PUBLICATIONS

Kar "Skeletal Tracking Using Microsoft Kinect" Methodology 1 pp. 1-11 (2010).
(Continued)

*Primary Examiner* — Kenny A Cese

(57) ABSTRACT

A subject support (14) is configured to dock with a medical imaging device (50) with a fixed spatial relationship between the docked subject support and the medical imaging device. A patient positioning device includes a range camera (10) that acquires a two-dimensional (2D) range image of a human imaging subject (12) disposed on a subject support (14). The range image has pixel values corresponding to distances from the range camera. An electronic processor (16) is programmed to perform a positioning method to determine a reference point on or in the human subject in a frame of reference ($F_S$) of the subject support from the 2D range image. This reference point is translated to a frame of reference ($F_D$) of the imaging device based on a priori
(Continued)

known spatial relationship of the medical imaging device and the docked subject support. Using 3D models, the loading process may be simulated.

13 Claims, 5 Drawing Sheets

(51) Int. Cl.
*A61B 5/11* (2006.01)
*A61B 5/00* (2006.01)
*G06T 3/00* (2006.01)
*G06T 7/00* (2017.01)

(52) U.S. Cl.
CPC .......... *G06T 3/0093* (2013.01); *G06T 7/0012* (2013.01); *G06T 7/344* (2017.01); *G06T 2207/10028* (2013.01); *G06T 2207/10088* (2013.01); *G06T 2207/30004* (2013.01); *G06T 2207/30196* (2013.01)

(58) Field of Classification Search
CPC . G06T 2207/10028; G06T 2207/30004; G06T 2207/30196; G06T 2207/10088; G06T 7/0012
See application file for complete search history.

(56) References Cited

U.S. PATENT DOCUMENTS

| | | |
|---|---|---|
| 2011/0002444 A1 | 1/2011 | Schmitt et al. |
| 2013/0281818 A1* | 10/2013 | Vija ........................ A61B 6/467 600/407 |
| 2014/0046342 A1* | 2/2014 | Hellier .................. A61B 34/10 606/130 |
| 2015/0002419 A1* | 1/2015 | White .................. G06V 40/103 345/173 |
| 2015/0035942 A1 | 2/2015 | Hampton et al. |
| 2015/0265852 A1 | 9/2015 | Meir et al. |
| 2015/0306340 A1 | 10/2015 | Giap et al. |
| 2017/0220709 A1* | 8/2017 | Wan ..................... A61N 5/1048 |
| 2018/0014745 A1 | 1/2018 | Senegas et al. |

OTHER PUBLICATIONS

International Search Report and Written Opinion (dated Feb. 9, 2018).

* cited by examiner

INTELLIGENT MODEL BASED PATIENT POSITIONING SYSTEM FOR MAGNETIC RESONANCE IMAGING

CROSS REFERENCE TO RELATED APPLICATIONS

This application is a U.S. national phase application of International Application No. PCT/EP2017/076137 filed on Oct. 12, 2017, which claims the benefit of IN Application Serial No. 201641034779 filed on Oct. 12, 2016 and is incorporated herein by reference.

FIELD

The following relates generally to the medical imaging arts, patient positioning arts, magnetic resonance imaging arts, and related arts.

BACKGROUND

An important step in magnetic resonance imaging (MRI) is the proper positioning of the patient. This entails selecting a reference point on the patient, which will be positioned in the isocenter of the magnet. In a known approach, the reference point selection is performed using one or more lasers mounted in fixed position relative to the MRI device (for example, mounted on the MRI device at the entrance to the magnet bore). These lasers project alignment patterns (e.g. alignment lines or crosshairs) onto the patient. The MRI technician moves the subject support (e.g. table top of a patient couch) to locate the desired reference point of the patient at the center of the projected laser alignment pattern, thus selecting that point as the reference. As the projection lasers have a fixed position relative to the MRI device (and hence relative to the magnet isocenter), the reference point on the patient has a known location in the frame of reference of the magnet (e.g. is located at a known distance from the magnet isocenter). The table top is then moved into the magnet bore, with all table top movements being referenced to this known magnet frame of reference. The magnet isocenter acts as the centre of gradient, the magnetic field strength increases and decreases based on isocenter position. The non-linear distortions are avoided by accurate positioning of gradient isocenter.

The following discloses a new and improved systems and methods.

SUMMARY

In one disclosed aspect, a patient positioning device comprises a range camera, an electronic processor, and a non-transitory storage medium storing instructions readable and executable by the electronic processor to perform a positioning method including: receiving a range image acquired by the range camera of a human subject and a subject support on which the human subject is disposed; and, using the range image, determining a reference point on or in the human subject in a frame of reference (FS) of the subject support.

In another disclosed aspect, a patient positioning method is disclosed. A range image is acquired of a human subject disposed on a subject support using a range camera. A reference point is determined on or in the human subject in a frame of reference of the subject support using the range image. In a radio frequency shielded magnetic resonance imaging (MRI) examination room, the subject support is docked with an MRI device and the human subject is positioned in the MRI device using the reference point on or in the human subject translated from the frame of reference of the subject support to a frame of reference of the MRI device. Advantageously, the acquiring of the range image and the determining of the reference point on or in the human subject in the frame of reference of the subject support using the range image can be performed at a location outside of the radio frequency shielded MRI examination room.

In another disclosed aspect, a patient positioning device comprises: a range camera configured to acquire two-dimensional (2D) range images having pixel values corresponding to distances from the range camera; a subject support configured to dock with a medical imaging device (50) with a fixed spatial relationship between the docked subject support and the medical imaging device; an electronic processor; and a non-transitory storage medium storing instructions readable and executable by the electronic processor to perform a positioning method to determine a reference point on or in a human subject in a frame of reference of the medical imaging device from a 2D range image acquired by the range camera of the subject support and the human subject disposed on the subject support.

One advantage resides in providing for patient positioning respective to an imaging device without being in the imaging examination room that contains the MRI device or other medical imaging device.

Another advantage resides in providing for more accurate patient positioning respective to an imaging device.

Another advantage resides in providing for patient positioning without the use of lasers or other high-intensity radiation.

Another advantage resides in providing for patient positioning with reduced stress to the patient.

Another advantage resides in providing for patient positioning with reduced likelihood of patient-bore collision.

Another advantage resides in providing for patient positioning in which the reference point is located inside the patient.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Existing approaches for positioning a patient for an MRI session or other type of medical imaging session have certain disadvantages. The use of alignment projection lasers attached to or in fixed position respective to the MRI device means that the patient must be positioned at or near the bore entrance, i.e. inside the MRI examination room. This places the patient and technician in close proximity to the strong magnetic field, and also adversely affects patient throughput since the MRI device cannot be performing imaging of another patient during the patient positioning process. Furthermore, the MRI examination room may not be well lit, and/or may be intimidating to the patient.

Another disadvantage with existing patient positioning systems is that the alignment projection laser produces relatively high intensity radiation that may disturb the patient, who is often already anxious due to the impending MRI session. In some cases, the high intensity laser light can be uncomfortable (or even damaging to) the patient's eyes if the laser beam is inadvertently directed into the eyes. This can be prevented by having the patient wear a blindfold during positioning, but this is likely to further increase patient anxiety.

Another disadvantage with existing patient positioning systems is that the alignment process only delineates the single reference point chosen with the assistance of the alignment projection lasers. This can lead to problems such as potential for collision of the patient with the bore wall when the patient is inserted into the magnet bore.

Another disadvantage with existing patient positioning systems is that the reference point must be located on the exterior of the patient, even though the actual imaging target may be an internal organ.

Another disadvantage is the relatively high cost of typical external laser alignment systems. Setup and alignment of the external lasers with the MRI or other medical imaging device is also labor-intensive.

Figure 1:
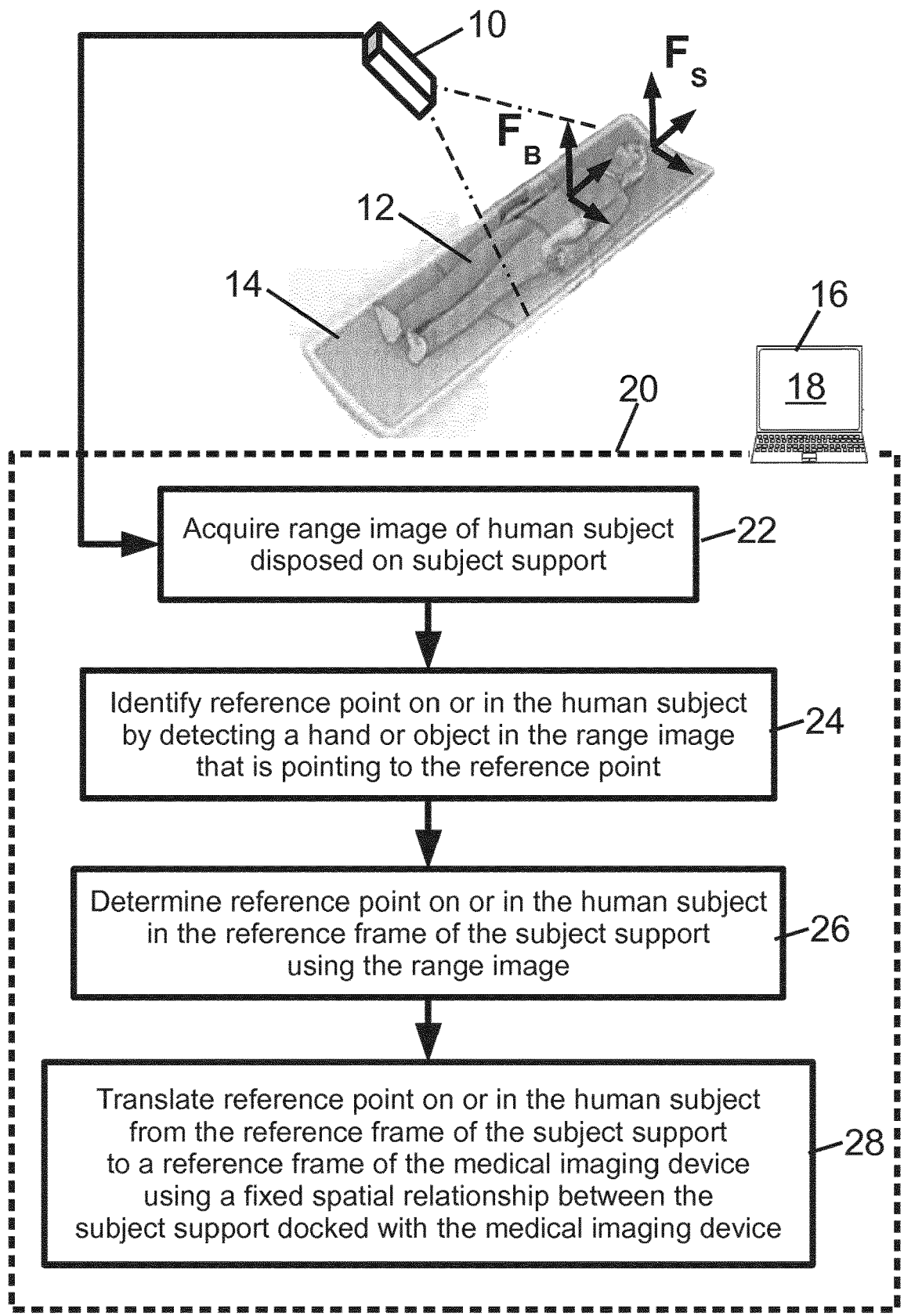
FIG. 1 diagrammatically illustrates a patient positioning device including a range camera.

With reference to FIG. 1, a patient positioning device is disclosed, which can be located outside of the MRI examination room and which does not employ alignment projection lasers. The patient positioning device employs a range camera 10 to acquire a range image of a human subject 12 to be imaged (e.g. an MRI patient) and a subject support 14 on which the human subject is disposed. A computer or other electronic data processing device 16 has a display 18 and an electronic processor and a non-transitory storage medium (details not shown) storing instructions readable and executable by the electronic processor to perform a positioning method 20 (diagrammatically indicated in FIG. 1) including the operation 22 of receiving the range image acquired by the range camera 10 of the human subject 12 and a subject support 14 on which the human subject is disposed, and, using the range image, determining a reference point on or in the human subject in a frame of reference of the subject support. The non-transitory storage medium may, by way of non-limiting illustrative example, include a hard disk or other magnetic storage medium, an optical disk or other optical storage medium, a solid state drive, flash memory or other electronic storage medium, various combinations thereof, or so forth.

In the illustrative method 20, the reference point determination includes the operation 24 of identifying a reference point on the human subject by detecting a hand or object (imaged) in the range image that is pointing to the reference point. This advantageously enables the technician or other medical imaging device operator to perform the reference point identification simply by pointing to the reference point. (An example of this is described later herein with reference to FIG. 3). In an operation 26, the reference point on or in the human subject is determined in the reference frame of the subject support using the range image. In an operation 28, the reference point on or in the human subject is translated from the reference frame of the subject support to a reference frame of the medical imaging device. In one embodiment, the operation 28 is done using an a priori known fixed spatial relationship between the subject support docked with the medical imaging device. The operation 28 is described in further detail later herein with reference to FIG. 5.

The range camera 10 is a camera that generates a range image. A range image comprises a two-dimensional (2D) image in which each pixel has a depth value. Thus, the range image captures three-dimensional (3D) information about the imaged subject. Said another way, a range image acquired by the range camera 10 has pixel values corresponding to distances from the range camera 10. Range cameras may employ various technologies to generate the range (i.e. depth) value for each pixel, such as light coding technology employed in the range camera component of the Kinect™ multi-sensor device (available from Microsoft Corporation), sheet of light triangulation, time-of-flight depth coding, or so forth. In addition to the Kinect™ device, as further examples some other suitable range cameras are available from Orbbec 3D Tech. Intl. Inc. and Intel Corporation (Intel® RealSense™ Camera). Commercial range cameras typically operate in the infrared, although range cameras operating in other wavelength ranges are also available.

Figure 2:
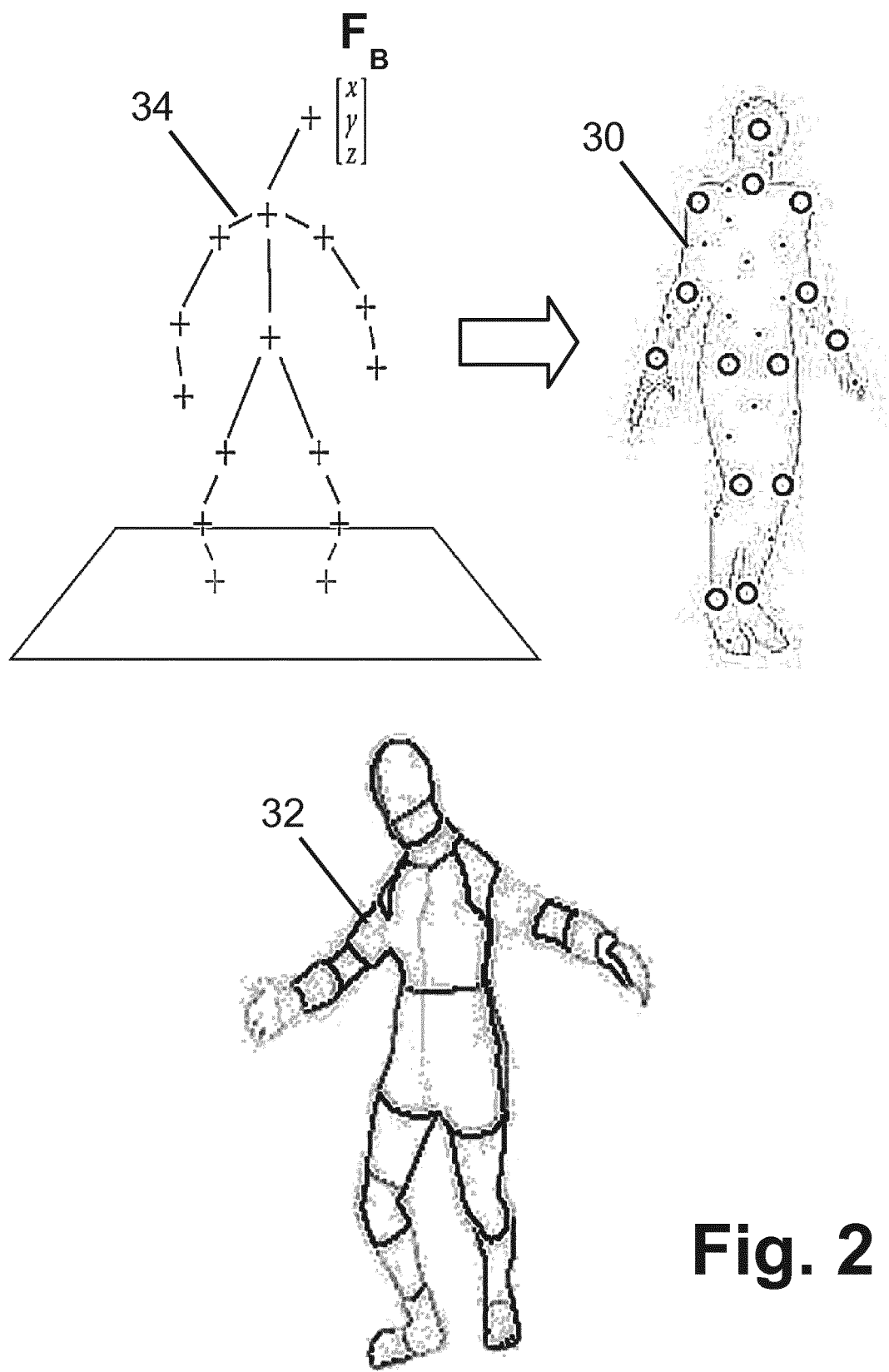
FIG. 2 diagrammatically illustrates a patient modeling process in which a 3D generic human body model is warped to generate a 3D human subject model that is aligned with the range image of the human subject acquired by the device of FIG. 1.

With reference to FIG. 2, the reference position can be located in 3D from the 3D information contained in the range image. However, although the range image contains 3D information, this information is limited to the exterior surface of the imaging subject 12. In some embodiments, this is sufficient as it enables identifying a reference point on the visible exterior of the subject, thus providing capability comparable with existing laser projection positioning systems. However, the range image can be exploited in conjunction with anatomical modeling to provide additional information, which can have various uses such as identifying the reference point as a point inside the subject, and/or enabling simulation of the subject loading process to detect a potential subject-bore collision situation. In one embodiment, depicted in FIG. 2, a 3D generic human body model 30 is warped to generate a 3D human subject model 32 that is aligned with the range image of the human subject 12 disposed on the subject support 14. In the illustrative example of FIG. 2, the warping is performed by skeletal tracking of a skeletal representation 34 of the human subject model 32. In skeletal tracking, the human body is represented by a number of joints making up the skeletal representation 34 and representing body parts such as head, neck, shoulders, and arms. In FIG. 2, this is diagrammatically indicated by open circles in the 3D human subject model 32 each representing a joint indicated by a plus sign in the skeletal representation 34. Each joint is represented by its 3D coordinates in a body frame of reference $F_B$ of the human subject (the plus sign markers). The equivalent representation of joints are represented as markers in generic human subject model 30 (the open circle markers). The generic human subject model 30 acts as template model. The 3D coordinates (marker coordinates) are warped based on real-time 3D coordinates acquired from the range image to generate the 3D human subject model 32. The intermediate body parts are estimated and mapped on the adapted 3D human subject model 32. The estimated body parts may be classified as regions of interest based on predefined MRI scan protocols. Based the anatomical region for scan corresponding region of interest is highlighted to define the reference point. In one approach, the region of interest representation on the 3D human subject model 32 is formed using per-pixel body part recognition using the range image. The per-pixel distribution may be computed using mean shift by evaluating each pixel separately. The per-pixel distribution is used to segment the region of interest in the resultant 3D human subject model 32. The region of interest can be distribution or same pixel value or combination of pixel values based on the region for scan. Some suitable skeletal tracking techniques for warping the 3D generic human body model 30 to generate the 3D human subject model 32 are described, for example, in Kar, "Skeletal tracking using microsoft kinect" Methodology 1 pp. 1-11 (2010).

It should be noted that the 3D generic human body model 30 is not necessarily generic to all human bodies. For example, it is contemplated to have different 3D generic human body models for male and female, and/or for children (possibly of various ages) versus adults, and/or for different body mass index (BMI) values, and/or so forth. In this case, determining the reference point further includes selecting one of the 3D generic human body models for use in the warping based on a human body class input received by the computer 16 as part of the MRI examination setup process.

In the case of MRI examination preparation in which the MRI examination will use local coils or coil arrays placed on the imaging subject 12, the range image is preferably acquired in operation 22 before coil placement for precise patient model adaptation with appropriate patient position for mapping.

With the 3D human subject model 32 generated, the reference point may be generated in various ways. In an automated approach, the reference point is placed at the center of the region of interest in the 3D human subject model 32. In this approach the region of interest may be identified by the technician pointing to it while the range image is acquired, or the region of interest may be determined automatically based on information entered during setup of the MRI examination, e.g. entry of the reason for examination. The reference point is typically the center of the field of view (FOV) for MRI scan acquisition. In another embodiment, a user-defined reference point can be set manually.

Figure 3:
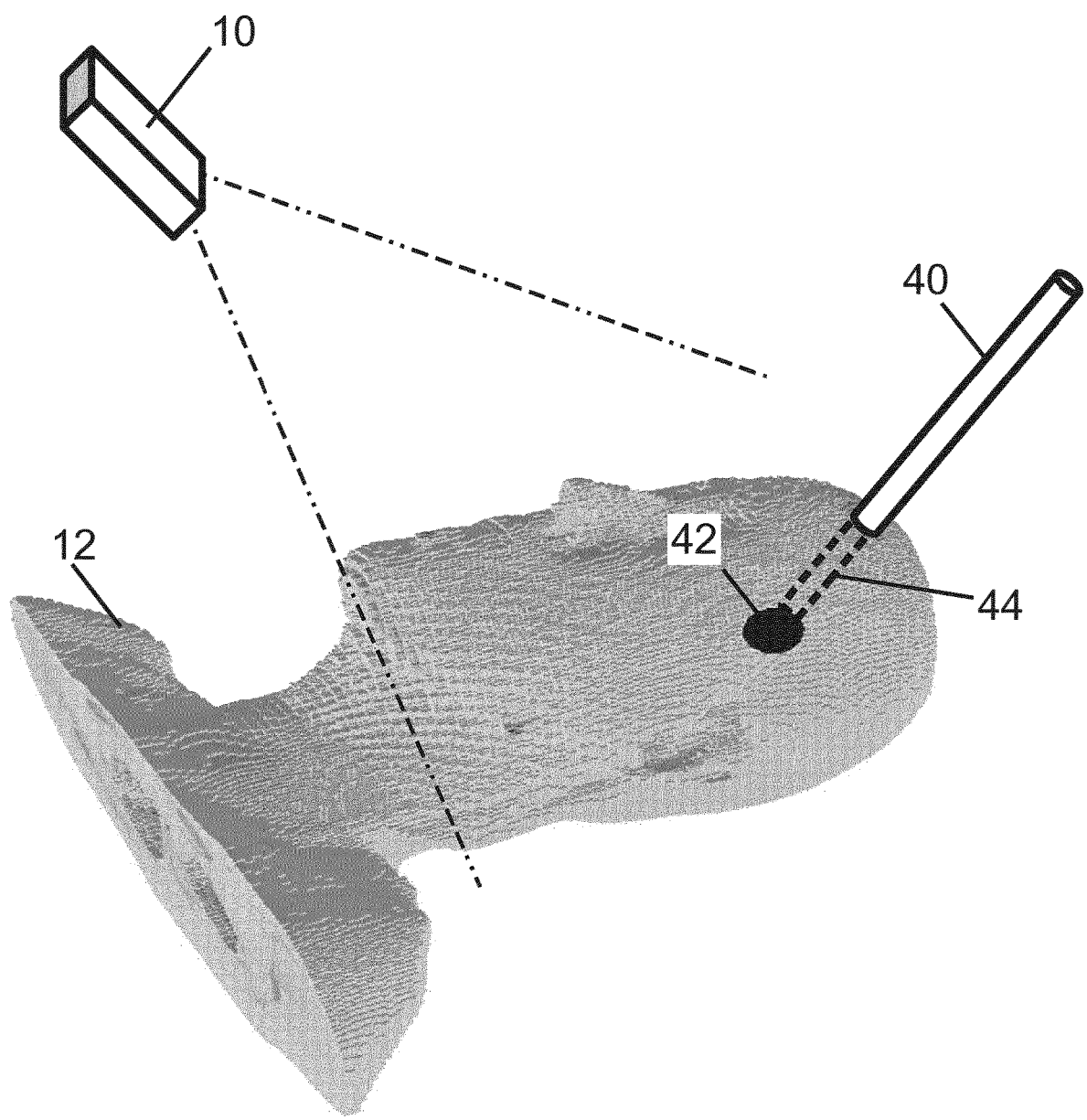
FIG. 3 diagrammatically illustrates use by the imaging technician of a hand or object (namely a rod in FIG. 3) for identifying the reference point on the human imaging subject.

With reference to FIG. 3, an illustrative example of the operation 24 is described. In this example, a rod 40 is used by the MRI technician to point to the reference point. In one embodiment, the computer 16 analyzes the range image to detect the rod 40 is pointing to the head region, and automatically places a brain imaging reference point 42 at the center of the brain region of interest. This approach is semi-automated in that the computer 16 calculates the brain imaging reference point 42 as the center of the brain region of interest, so that the MRI technician need only direct the rod 40 to generally identify the head of the patient. In another embodiment, the computer 16 generates a projection 44 of the rod into the (model of) the human head to locate the reference point 42. In this embodiment a representation such as that of FIG. 3 may be displayed on the display 18 of the computer 16 and the user may operate a slider or other graphical user interface (GUI) dialog control to adjust the depth of the projection 44. Advantageously, by such approaches the reference point can be identified inside the human body; by contrast, laser projection patient positioning devices typically locate the reference point on the surface of the human body. Since MRI and other medical imaging techniques are imaging the interior of the human body, the ability to locate the reference point inside the human body provides better positioning of the region of interest at the isocenter of the MRI magnet (or, more generally, provides better positioning of the region of interest at the center of the examination region of the medical imaging device).

With returning reference to FIG. 1, in the operation 26 the reference point on or in the human subject 12 is determined in the reference frame of the subject support 14. In a suitable approach, there exists reference features on subject support 14 and markers on 3D human subject model 32 to depict patient position with respect to table. The reference features on the subject support 14 should be imaged by the range image, and accordingly may be dedicated features such as molded grooves or ridges (providing range variation) or features such as corners off the subject support. The overall spatial coordinates of patient table and patient model is extracted in this process. FIG. 1 indicates the aforementioned body frame of reference $F_B$ of the human subject 12, and also a subject support frame of reference $F_S$ of the subject support 14. In a preferred approach, the two frames of reference are both Cartesian with x-, y-, and z-directions that are parallel in the two frames of reference $F_B$, $F_S$. In this case, translating from the body frame of reference $F_B$ to the subject support frame of reference $F_S$ merely entails a translation operation:

$$x_S = x_B + \Delta x_{BS}$$
$$y_S = y_B + \Delta y_{BS}$$
$$z_S = z_B + \Delta z_{BS} \qquad (1)$$

where the reference point in the body reference frame $F_B$ is given by the Cartesian coordinates ($x_B$, $y_B$, $z_B$), the reference point in the subject support reference frame $F_S$ is given by the Cartesian coordinates ($x_S$, $y_S$, $z_S$), and the factors $\Delta x_{BS}$, $\Delta y_{BS}$, and $\Delta z_{BS}$ are the translational shifts determined from the range image, and more particularly by the x-, y-, and z-directional distances between the body and subject support reference markers. Rotational adjustments can be similarly added if the x-, y-, and z-directions are not parallel in the two frames of reference.

Figure 4:
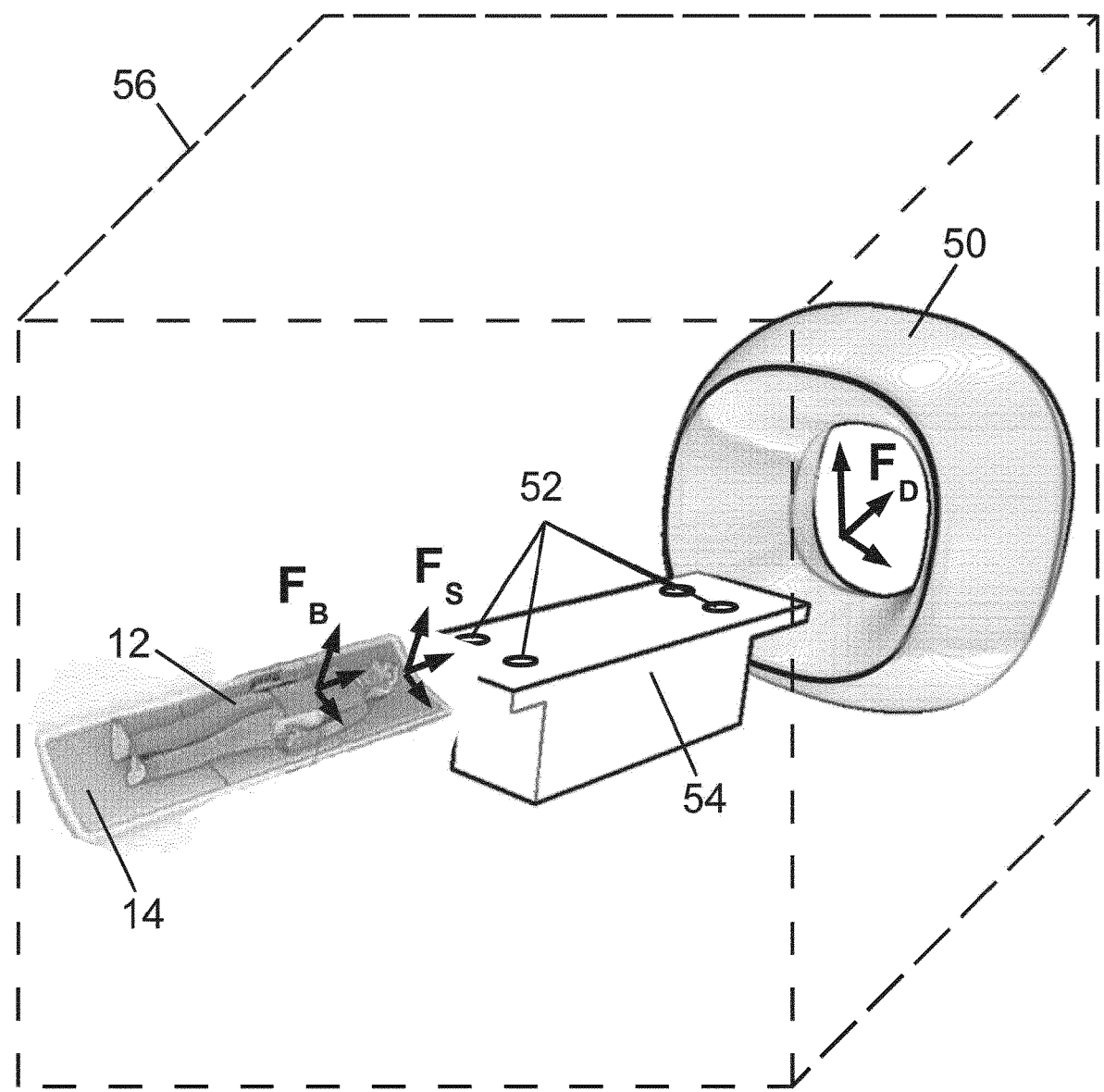
FIG. 4 diagrammatically shows docking of the subject support carrying the patient with the magnetic resonance imaging (MRI) device.

With continuing reference to FIG. 1 and with further reference to FIG. 4, the operation 28 translates the reference point from the frame of reference $F_S$ of the subject support to a frame of reference $F_D$ of a medical imaging device 50. It is assumed here that the subject support 14 is designed to dock with the medical imaging device 50 with some defined spatial between the two components 14, 50 in the docked position. For example, in a common arrangement the subject support 14 includes mating features (not shown) that mate with mating features 52 of the medical imaging device 50 to dock the subject support 14 to the medical imaging device 50. In some embodiments, the subject support 14 is a tabletop that has pegs, holes, or other mating features that mate with the mating features 52 comprising mating holes, pegs, or the like of a robotic patient loading couch 54 of the MRI imaging device 50. In a variant embodiment (not shown), the subject support is a dockable couch or gurney, and the couch or gurney has wheels and a docking connector for connecting the couch or gurney to the MRI device.

Assuming the two frames of reference $F_S$, $F_D$ are Cartesian with parallel respective x-, y-, and z-directions, translation of the reference point in the frame of reference $F_S$ of the subject support 14 to the frame of reference $F_D$ of the MRI device 50 is a straightforward translation:

$$x_D = x_S + \Delta x_{SD}$$
$$y_D = y_S + \Delta y_{SD}$$
$$z_D = z_S + \Delta z_{SD} \quad (2)$$

where the reference point in the subject support reference frame $F_S$ is given by the Cartesian coordinates $(x_S, y_S, z_S)$, the reference point translated to the imaging device reference frame $F_D$ is given by the Cartesian coordinates $(x_D, y_D, z_D)$, and the factors $\Delta x_{SD}$, $\Delta y_{SD}$, and $\Delta z_{SD}$ are the translational shifts known a priori due to the fixed docked position of the subject support 14 respective to the medical imaging device 50.

It should be noted that in some embodiments the patient positioning method 20 of FIG. 1 can be performed entirely outside of the MRI examination room containing the MRI device 50. As is known in the art, the MRI device 50 is typically located in a radio frequency shielded magnetic resonance imaging (MRI) examination room 56, so as to suppress radio frequency (RF) interference from outside reaching the MRI device 50 and so as to block the magnetic and RF and magnetic fields generated by the MRI device 50 from interfering with electronic equipment and devices located outside of the shielded. MRI examination room 56. The disclosed approach leverages the subject support 14 and its frame of reference $F_S$ to provide a "bridge" for translating the reference point on the imaging subject 12 from the body reference frame $F_B$ to the imaging device reference frame $F_D$. This allows the patient (or, more generally, imaging subject) to be positioned on the subject support 14, imaged using the range camera 10, and the reference point determined in the subject support reference frame $F_S$. As this subject support reference frame $F_S$ has an a priori-known spatial relationship with the medical imaging device reference frame $F_D$, each of the operations 22, 24, 26, 28 can be performed outside of the shielded MRI examination room 56. This can increase patient throughput in an MRI laboratory as while one patient is being imaged in the shielded MRI examination room 56, the next patient can be prepared for examination including identifying the reference point in an adjacent room. Moreover, this can be done using the range camera 10, without the need for using a laser projection system with its potential for introducing ocular discomfort.

A range camera may additionally or alternatively be provided in the MRI examination room. In the alternative case in which there is only one range camera which is located in the MRI examination room, the patient positioning method 20 is suitably performed in the MRI examination room. In embodiments in which two range cameras are provided (one outside the MRI examination room and the other inside the MRI examination room), the patient positioning method 20 can be performed outside the MRI examination room and the result confirmed using the camera inside the MRI examination room, e.g. by repeating the patient modeling process of FIG. 2 using a range image acquired using the range camera in the MRI examination room to correct for any changes in patient positioning that may have occurred as the patient is moved into the MRI examination room. If a range camera is located inside the MRI examination room, then it should be suitably shielded to control RF interference.

The 3D coordinates of the reference point passed from the patient positioning process can also be used as an input for other examination setup actions, such as defining the slice thickness for the region of interest and different post-processing steps in MR image based application like diffusion weighted imaging.

Figure 5:
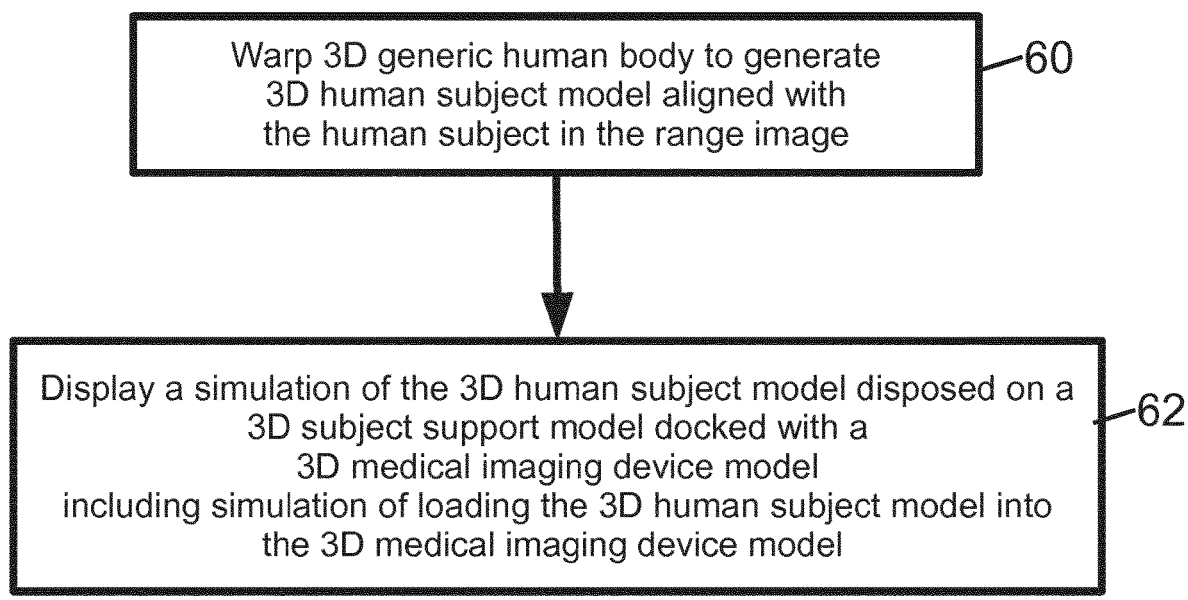
FIG. 5 diagrammatically shows a patient loading simulation process.

With reference to FIG. 5, as another example it is also contemplated to provide a graphical simulation of the subject loading process, so as to enable the technician to easily detect any potential patient-bore collisions. In one implementation, a graphical virtual 3D model of MRI device 50, along with a 3D model of the subject support 14 and the aforementioned 3D human subject model 32, is stored on the non-transitory storage medium of the computer 16 to enable graphical visualization of the entire patient loading process (and optionally the entire image acquisition process) on the display 18 of the computer 16. The 3D MRI device model represents the actual MRI device 50, and the adapted 3D human subject model 32 is placed over the 3D model of the subject support 14 to provide a visualization of the entire system. The reference point coordinates defined on the 3D human subject model 32 is translated into the 3D model of the MRI device 50. The coordinates of the reference point which are acquired using the range camera 10 serve as reference between the simulation system and the actual setup. The simulation of the loading process can be performed to visualize the field of view of the scan and perform a pre-acquisition check. The 3D coordinates of the reference point are passed to the MRI device 50 which positions the subject support 14 automatically to the center of scanner bore or the field of view. FIG. 5 depicts the loading simulation process, including operation 60 comprising the warping of the 3D generic human body model 30 to generate the 3D human subject model 32 as already described, e.g. with reference to FIG. 2, and an operation 62 comprising displaying a simulation of the 3D human subject model 32 disposed on a 3D subject support model (representing subject support 14) docked with a 3D medical imaging device model (representing the MRI device 50). The simulation includes simulation of loading the 3D human subject model 32 into the 3D medical imaging device model It is noted that the specific implementation of frame of reference transfers, i.e. from the body reference frame $F_B$ to the subject support reference frame $F_S$ via Equation (1) followed by from the support reference frame $F_S$ to the MRI device reference frame $F_D$ via Equation (2), is merely an illustrative example, and other approaches can be employed.

For example, in an alternative embodiment the use body modeling as per FIG. 2 can optionally be omitted, and the reference point directly defined from the range image in the frame of reference $F_S$ of the subject support 14. This can be done since the subject support 14 is imaged in the range image, so its coordinate system can be used directly. This approach makes it more difficult to define a reference point inside (rather than on an imaged surface of) the subject 12, but an approach such as the described projection 44 can be used, employing a "typical" depth of the brain center. This approach also omits the body frame of reference $F_B$ and the modeling of FIG. 2, and accordingly the dynamic loading simulation aspect described with reference to FIG. 5 is not implemented.

Further, while described with reference to MRI, it will be appreciated that the disclosed patient positioning approaches can be used in conjunction with other medical imaging devices that employ (or can be modified to employ) a separable subject support that can be loaded with a next subject during imaging of a current subject. These include, by way of non-limiting illustrative example, transmission computed tomography (CT) imaging devices, positron emission tomography (PET) imaging devices, gamma cameras used for single photon emission computed tomography (SPECT), various hybrid medical imaging devices (e.g., PET/CT) and so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A positioning device for positioning a human subject disposed on a subject support relative to a medical imaging device, the positioning device comprising:
   a range camera;
   a display;
   a processor; and
   a non-transitory storage medium storing:
   a three-dimensional (3D) generic human body model representing a generic human body;
   a 3D medical imaging device model representing the medical imaging device;
   a 3D subject support model representing the subject support; and
   instructions readable and executable by the processor to perform a positioning of the human subject, wherein when executed by the processor, the instructions cause the processor to:
   receive a range image acquired by the range camera of the human subject and the subject support on which the human subject is disposed;
   warp the 3D generic human body model to generate a 3D human subject model that is aligned with the range image of the human subject disposed on the subject support;
   determine a reference point on or in the 3D human subject model in a frame of reference ($F_s$) of the subject support; and
   present on the display, a simulation of the 3D human subject model disposed on the 3D subject support model with the 3D subject support model aligned with the 3D medical imaging device model including simulation of loading the 3D human subject model into the 3D medical imaging device model.

2. The positioning device of claim 1, wherein warping the 3D generic human body model includes performing skeletal tracking.

3. The positioning device of claim 1, wherein the non-transitory storage medium stores a plurality of different 3D generic human body models for different classes of human bodies, and wherein determining the reference point further includes selecting one of the 3D generic human body models for use in the warping based on a human body class input received by the processor.

4. The positioning device of claim 1, wherein determining the reference point includes:
   detecting a pointer to the reference point in the range image.

5. The positioning device of claim 1, further comprising the subject support wherein the subject support includes mating features for mating the subject support with a medical imaging device.

6. The positioning device of claim 5, wherein the medical imaging device comprises a magnetic resonance imaging (MRI) device.

7. The positioning device of claim 1, wherein determining the reference point includes:
   determining a reference point on or in the 3D human subject model in a frame of reference ($F_B$) of the human subject; and
   translating the reference point on or in the 3D human subject model in the frame of reference of the human subject to the frame of reference ($F_s$) of the subject support using the range image in order to determine the reference point on or in the 3D human subject model in the frame of reference of the subject support.

8. The positioning device of claim 7, wherein
   the reference point on or in the 3D human subject model in the frame of reference of the human subject is determined from a positional relationship between a hand or object in the range image and the human subject in the range image.

9. A non-transitory computer readable medium storing instructions for positioning a human subject relative to a medical imaging device that, when executed by a processor, cause the processor to:
   receive a range image, acquired by a range camera, of the human subject and a subject support on which the human subject is disposed;
   warp a three-dimensional (3D) generic human body model, representing a generic human body, to generate a 3D human subject model that is aligned with the range image of the human subject disposed on the subject support;
   determine a reference point on or in the 3D human subject model in a frame of reference ($F_s$) of the subject support; and
   present on a display, a simulation of the 3D human subject model disposed on a 3D subject support model, representing the subject support, with the 3D subject support model aligned with a 3D medical imaging device model, representing the medical imaging device, wherein the simulation includes simulation of loading the 3D human subject model into the 3D medical imaging device model.

10. The non-transitory computer readable medium of claim 9, wherein execution of the instructions further cause the processor to:
    translate the reference point from the frame of reference ($F_s$) of the subject support to a frame of reference ($F_D$) of the medical imaging device prior to presenting the simulation on the display.

11. The non-transitory computer readable medium of claim 9, wherein warping the 3D generic human body model includes performing skeletal tracking.

12. The non-transitory computer readable medium of claim 9, wherein determining the reference point includes detecting a pointer to the reference point in the range image.

13. The non-transitory computer readable medium of claim 9, wherein the medical imaging device comprises a magnetic resonance imaging (MRI) device.

* * * * *